United States Patent
Pichon et al.

(12)

(10) Patent No.: US 8,736,688 B2
(45) Date of Patent: May 27, 2014

(54) METHOD AND DEVICE FOR ANALYZING THE OPTICAL QUALITY OF A TRANSPARENT SUBSTRATE

(75) Inventors: Michel Pichon, Gouvieux (FR); Franc Davenne, Thourotte (FR)

(73) Assignee: Saint-Gobain Glass France, Courbevoie (FR)

( * ) Notice: Subject to any disclaimer, the term of this patent is extended or adjusted under 35 U.S.C. 154(b) by 73 days.

(21) Appl. No.: 13/637,318

(22) PCT Filed: Mar. 28, 2011

(86) PCT No.: PCT/FR2011/050675
§ 371 (c)(1),
(2), (4) Date: Sep. 25, 2012

(87) PCT Pub. No.: WO2011/121219
PCT Pub. Date: Oct. 6, 2011

(65) Prior Publication Data
US 2013/0010175 A1 Jan. 10, 2013

(30) Foreign Application Priority Data
Apr. 1, 2010 (FR) ...................... 10 52477

(51) Int. Cl.
*H04N 5/225* (2006.01)
(52) U.S. Cl.
USPC .................... 348/207.99; 348/92
(58) Field of Classification Search
CPC ...................................................... H04N 5/225
USPC ............... 348/187, 188, 189, 190, 86, 92–95; 382/294
See application file for complete search history.

(56) References Cited

U.S. PATENT DOCUMENTS

| 5,175,601 | A | 12/1992 | Fitts |
| 7,706,634 | B2 * | 4/2010 | Schmitt et al. ................ 382/294 |
| 2006/0158664 | A1 | 7/2006 | Koh et al. |
| 2009/0051929 | A1 | 2/2009 | Koh et al. |
| 2010/0045955 | A1 * | 2/2010 | Vladimirsky et al. .......... 355/70 |
| 2011/0187855 | A1 | 8/2011 | Pichon et al. |

FOREIGN PATENT DOCUMENTS

FR 2 898 969 9/2007

OTHER PUBLICATIONS

International Search Report Issued Jun. 30, 2011 in PCT/FR11/050675 Filed Mar. 28, 2011.

* cited by examiner

*Primary Examiner* — Tuan Ho
(74) *Attorney, Agent, or Firm* — Oblon, Spivak, McClelland, Maier & Neustadt, L.L.P.

(57) ABSTRACT

A device for analyzing a transparent surface of a substrate including a reference pattern facing a surface of the substrate to be measured. The reference pattern is formed on a support of short and long extents. A camera is provided for taking at least one image of the reference pattern distorted by the measured substrate. A reference pattern illumination system and a processor for processing the image and digital analysis are connected to the camera. The support is of oblong shape and the reference pattern is a one-directional pattern that extends along the shortest extent of the support. The pattern is transversely periodic to the short extent, and the camera is a linear camera.

14 Claims, 1 Drawing Sheet

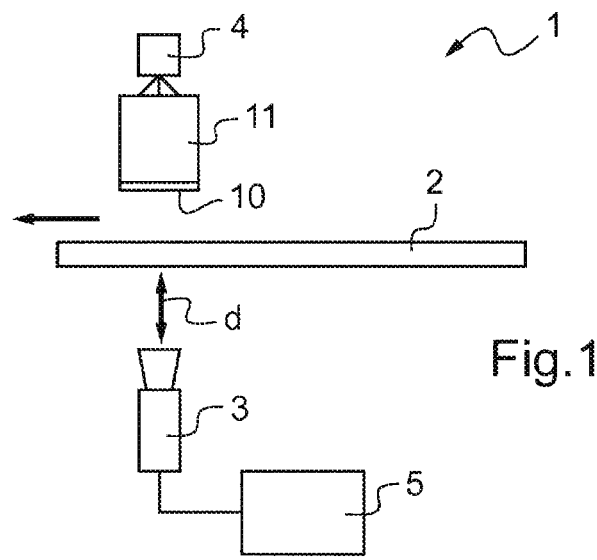
Fig.1
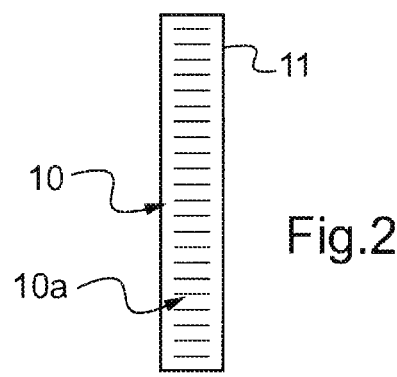
Fig.2
Fig.3
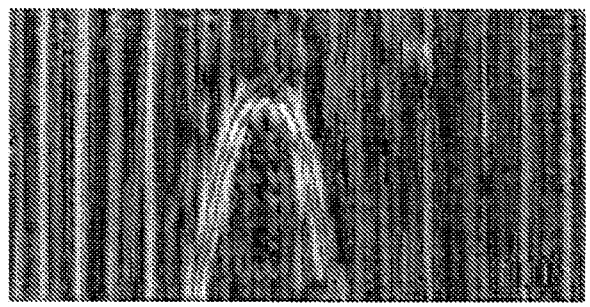

METHOD AND DEVICE FOR ANALYZING THE OPTICAL QUALITY OF A TRANSPARENT SUBSTRATE

The invention relates to a device for analyzing the optical quality of a transparent substrate, making it possible in particular to detect distorting optical defects present either on the surface of this substrate or in its bulk.

The optical defects of transparent substrates are characterized by the optical distortions that they cause when these substrates are in a use situation such as for example in automotive glazing, architectural glazing, plasma or LCD display screens, etc.

Detecting optical defects in these substrates at the end of the manufacturing line, although this may prove to be effective in terms of quality control, is often very expensive as it is carried out on a finished product, ready for shipment. It is clearly preferable to detect these defects as soon as possible, i.e. during formation of the substrate that will serve for producing the finished product.

Since these substrates are often produced using drawing or extrusion processes, to produce them in the form of a continuous ribbon, it is necessary to have an inspection tool which fits with this tool on an industrial line, on a continuous ribbon, for exhaustive inspection and without the need to modify the production line.

In the case of a float glass formed by drawing, defects causing optical distortions appear in only one direction, parallel to the edges of the sheet, and correspond to the signature of the forming process, the intensity of these defects being of greater or lesser importance depending on the quality of the forming process.

The techniques usually employed for detecting and evaluating the defects typically consist:

either in observing the defects visually by using on-line shadowgraph techniques consisting in illuminating the sheet using a powerful point light source and in collecting, after transmission through the substrate, the light flux on a screen. Visual analysis of this image makes it possible most of the time to detect the defects that have a strong gradient, i.e. intense narrow defects that provide an image of sufficient contrast to be observable, without providing precise information about the intensity of these defects. A sample then has to be taken;

either by regularly taking a glass specimen of large size and visually analyzing it off line;

or by taking small specimens that may be measured using suitable measurement devices.

These inspection techniques are not very effective, not exhaustive, imprecise, involve many operators and in particular detrimentally affect the production costs. They are not very effective in the case of defects of moderate or low intensity. The measured intensities are rarely checkable.

Moreover transparent substrate inspection techniques are commercially available which make it possible to detect optical defects by measurements in transmission based on the observation of regular reference patterns throughout the substrate.

The document U.S. Pat. No. 6,509,967 describes a method for detecting optical defects based on analyzing the distortions of a two-dimensional reference pattern observed in transmission. In the case of defects, the image of the reference pattern is distorted, and the distortion of numerous points of the image is measured so as to deduce therefrom, after prior calibration, the optical power along two directions, the values of which are representative of the presence or absence and the magnitude of said defects. This document insists on the need for studied coupling of the reference pattern relative to the camera responsible for the image acquisition in transmission. Each line of the reference pattern must correspond precisely to an integral number of lines of pixels of the camera.

However, the method of this United States patent requires the characteristics of the reference pattern (its dimensions, its shapes and its position) and of the camera (number of pixels, distance with respect to the reference pattern, etc.) to be known or adapted so as to ensure that the pattern of the reference pattern is suitably aligned with the pixels of the camera. Such an alignment is restricting and rarely possible in an industrial environment (poor regularity of the reference pattern, expansion of the reference pattern with the variations in temperature over the day, floor vibrations, etc.).

Document U.S. Pat. No. 6,208,412 provides another measurement method in which a one-dimensional reference pattern is observed in transmission. The measurement device of the above document uses a projector to generate a reference pattern which forms, on a large screen, always substantially greater than the size of the glazing panel to be measured (typically 2×3 m), a one-dimensional periodic pattern which can vary in time, and also a matrix camera that displays the reference pattern through the glazing panel to be analysed. The reference pattern must have graduated shades of grey, i.e. it must not have sharp local contracts.

The device described in the latter document, although it may be satisfactory in the laboratory or on edge of a production line for quality control by taking samples, cannot however be used for on-line inspection on a continuously running tape, in the context of an inspection which has to be exhaustive without the possibility of momentarily stopping the glass.

The incorporation of a projector and a large screen on an industrial line is also rarely possible or desirable, for lack of space. Moreover, the image produced by a projector is in general not very bright. It is therefore essential to shield the screen from spurious ambient light by extensively covering it and even painting the floor black.

Finally, the measurement method described is a well-known phase-shifting method which consists, with the glazing panel stopped, in successively projecting several, typically four, reference patterns that are offset in space and in acquiring an image for each reference pattern position. This series of acquisitions is therefore very time-consuming and further extends the time during which the glazing panel is stopped. This mode of operation is incompatible with measuring on a constantly moving substrate.

Consequently, the device described in U.S. Pat. No. 6,208,412 and its measurement procedure are incompatible with measurement on an industrial line, on a constantly moving continuous substrate which is limited by an exhaustive inspection.

The Applicant was thus given the mission of designing a device for analyzing the optical quality of a transparent substrate that does not have the drawbacks of the abovementioned techniques and makes it possible to detect and quantify defects of this substrate in transmission, in an easy, precise and repetitive manner while still meeting all the constraints of implementation on an industrial line for inspection of the glass over its entire length, on a fixed or moving substrate and in particular by reducing the cost of glass conformity inspection on a production line. This innovative device must furthermore make it possible to use measurement methods that result in the analysis time being optimized.

To this end, one subject of the invention is a device for analyzing a transparent surface of a substrate comprising a reference pattern formed on a support facing the surface of the substrate to be measured, a camera for capturing at least one image of the reference pattern distorted by the measured substrate, a reference pattern illumination system and image processing/digital analysis means which are connected to the camera, characterized in that the support has an oblong shape of short and long extents, the reference pattern being unidirectional and consisting of a pattern that lies along the shorter extent of the support, the first pattern being periodic transverse to the short extent, and in that the camera is linear and is positioned so as to obtain a linear image in transmission of the reference pattern through the substrate along the long extent of the support.

According to particular embodiments, the device comprises one or more of the following features, taken individually or in any technically possible combination:
  the ratio of the long extent of the support to the short extent of the support is for example equal to or greater than 10, preferably equal to or greater than 20;
  the pattern comprises at least one line which has, along the short extent of the support, a width of between 0.1 mm and 5 cm, preferably between 1 mm and 2 mm;
  the pattern is composed of an alternating succession of light and dark lines;
  the support for the reference pattern consists of a panel back-lit by the illumination system;
  the support is, on its face turned towards the glazing panel to be measured, translucent and diffusing, such as a white plastic sheet;
  the illumination system is formed from a multitude of electroluminescent diodes;
  the substrate is placed between the reference pattern and the camera for a measurement in transmission;
  the support for the reference pattern is mounted so as to move relative to the substrate perpendicularly to the plane in which the substrate runs;
  the device comprises a mechanical raising/lowering system for moving the support for the reference pattern further away from or closer to the substrate, while still maintaining sufficient sharpness of the image of the reference pattern captured by the camera;
  the device comprises a memory in which suitable programs are recorded for:
    using the linear camera, taking a linear image in transmission of the illuminated reference pattern, the substrate or the reference pattern moving, one relative to the other, along a single running direction parallel to the direction of the defects and to the lines of the reference pattern;
    (1) acquiring the row of pixels of the linear image taken along the long extent of the reference pattern, without moving the camera relative to the reference pattern;
    (2) applying digital processing to the acquired row of pixels in order to calculate a representative quantity, for each pixel, of the effect of the substrate on the light transmitted by the substrate, for example the optical power of each pixel;
    (3) storing in memory the values of this quantity for each pixel of the row, and displaying an image of the row of pixels in which the color of each pixel is representative of this quantity;
    repeating the acquisition/processing/display cycle (1) (2)(3) several times in a periodic manner and stacking the images of the rows of pixels so as to reconstruct the image of a part of the substrate; and
    analyzing the reconstructed image by digital processing so as to deduce therefrom the position of the defects and to quantify their gravity.
  the row acquisition period is longer than the acquisition time for each row, for example 0.1 seconds or longer;
  each row is displayed after each step (2) so that the reconstructed image of a part of the substrate simulates a continuous running effect that will correspond to the display in real-time of a 2D map of the defects;
  the substrate is a continuous glass ribbon.

It will be recalled that a linear camera comprises a single video sensor delivering, as output signal, a single row of pixels. The sensor comprises a single receiver composed of several juxtaposed sensitive elements corresponding to the respective pixels of the output signal, the sensitive elements being aligned along a single row. Linear cameras are compact and provide swift acquisition.

The oblong shape of the support of the reference pattern accompanied by the use of a linear camera makes it possible highly advantageously to reduce the area occupied by the reference pattern and thus limit the space necessary for the device on a production line.

The magnitude of the patterns of the reference pattern and the position of the reference pattern, the glass and the camera are of course to be adapted to each type of measurement, this device being suitable for inspecting specimens a few centimeters in width, such as the inspection of a continuously running glass ribbon several meters in width. In the latter case, several camera/reference pattern systems will be combined in order to cover the entire width of the ribbon to be analyzed. For smaller substrates, the long extent of the support may correspond to the width of the substrate to be measured.

The ratio of the long extent of the support to the short extent of the support is for example equal to or greater than 10, preferably equal to or greater than 20.

It is also known that the perceived distortions, expressed in terms of optical magnification by a stationary observer placed on one side of the substrate, observed in transmission, vary with the distance between the substrate and the reference pattern which, optically speaking, acts as object. It should be noted that the optical power is defined, as is known, by the inverse of the focal length of the equivalent optical lens that would give, if positioned in place of the defect, the same magnification as that perceived by the observer.

Thus, to adapt the sensitivity of the device, i.e. to increase or reduce the distorting effect of a given optical defect, it is possible to modify the distance between the reference pattern and this defect, and therefore the substrate. This effect may be carried out using a mechanical raising/lowering system that moves the reference pattern further away from or closer to the substrate, while still maintaining sufficient sharpness of the image of the reference pattern captured by the camera. Since our device does not require a precise in-depth focusing of the camera onto the reference pattern, it is readily possible to double the sensitivity of this device by increasing the reference pattern-substrate distance by a factor of about 2. It is then possible for the device to be rapidly reconfigured, without performing further optical adjustments, so that it is suitable for a new range of defects characterized by different optical powers.

According to one feature, the pattern of the reference pattern is composed of an alternating succession of light and dark lines, preferably strongly contrasted (for example white and black lines) and of equal lengths, respectively. The width of the lines forming each pattern is in fact adapted to the measurement and defect width conditions. The width of the lines may thus be between 0.1 mm and 10 mm, preferably between 1 mm and 2 mm.

Furthermore, if the illumination system is associated directly with the reference pattern such as by back-lighting, the support panel for the reference pattern may then not exceed 5 cm in width, therefore considerably reducing the dimensions for installing the device of the invention compared with the existing ones.

As back-lit panel, the panel is, on its face turned towards the substrate to be measured, translucent and diffusing. For example, it is a white plastic sheet. This may also be a transparent substrate on which the reference pattern is printed. In this case, a second, translucent plate associated with the illumination will provide the luminous background necessary for the approximately uniform back-lighting of the reference pattern, although this uniformity is not critical.

Advantageously, and in particular in the case of back-lighting, the illumination system is formed from numerous light-emitting diodes. This illumination may be judiciously intensity-modulated over time so as, for example, to increase the life time thereof or to adapt it to the transmission of a relatively absorbent substrate.

To take a measurement in transmission, the substrate is positioned between the reference pattern and the camera.

The invention also relates to a method of analyzing a transparent or specular surface of a substrate using a device comprising a reference pattern formed on a support of oblong shape of short and long extents, a linear camera for taking at least one image of the pattern distorted by the measured substrate, a reference pattern illumination system, and image processing/digital analysis means that are connected to the camera, the method comprising steps consisting in:

using the linear camera, taking a linear image in transmission of the illuminated reference pattern, the substrate or the reference pattern moving, one relative to the other, along a single running direction parallel to the direction of the defects and to the lines of the reference pattern;

(1) acquiring the row of pixels of the linear image taken along the long extent of the reference pattern, without moving the camera relative to the reference pattern;

(2) applying digital processing to the acquired row of pixels in order to calculate a representative quantity, for each pixel, of the effect of the substrate on the light transmitted by the substrate, for example the optical power of each pixel;

(3) storing in memory the values of this quantity for each pixel of the row, and displaying an image of the row of pixels in which the color of each pixel is representative of this quantity;

repeating the acquisition/processing/display cycle (1) (2) (3) several times in a periodic manner and stacking the images of the rows of pixels so as to reconstruct the image of a part of the substrate; and analyzing the reconstructed image by digital processing so as to deduce therefrom the position of the defects and to quantify their gravity.

According to particular embodiments, the method also has one or more of the following features, taken individually or in any technically possible combination:

each line is displayed after each step (2) so that the reconstructed image of a part of the substrate simulates a continuous running effect that will correspond to the display in real-time of a 2D map of the defects;

the substrate is a continuous glass ribbon;

the line acquisition period is longer than the acquisition time for each row, for example 0.1 seconds or longer.

The rate of imaging of each line will be slaved to the rate of relative displacement of the substrate with respect to the reference pattern in order to prevent any overlap, in the running direction, of an image from one row of pixels to the next. To save time, it may be acceptable for the acquisition time for a line to be shorter than its processing time, this having the effect of not recording a known fraction of the substrate.

The analysis will then relate only to defects that pass beneath the camera for a time of the order of one second, while point defects, passing under the camera for a time of typically one tenth of a second will be detected only randomly.

In this way, by virtue of the device and the method of the invention, it is possible to carry out rapid and reliable inspection on a representative specimen of regularly spaced lines on the substrate. The entire substrate may thus be rapidly inspected, even if the spaces between the lines are not inspected. If it should be necessary for the spaces between the analysized lines also to be inspected, it would be advantageous to multiply the device by placing one or more identical devices downstream, all synchronized to analyze a different portion of the substrate, i.e. the spaces between the lines analyzed by the other devices, all the devices being preferably synchronized on the same image acquisition periodicity.

The digital processing of each line is carried out in a known manner. This involves for example extracting local phases of the row of pixels obtained using the linear camera and deducing therefrom phase variations in order not only to deduce the position of defects but also quantify them by measuring the deformation of the lines of the reference pattern from which a magnitude of the distortion or an optical power representative of the defects may be provided, thanks to an optical calculation model.

It should be noted that the digital phase extraction processing may be carried out, using the incidentally when known Fourier transform method.

It appears that the method according to the invention gives satisfactory results on industrial lines, without modifying the latter, for lower cost, and permits much more rapid inspection than in the prior art.

The device of the invention and the method of implementation may be applied to transparent substrates, such as monolithic or laminated, flat or curved, glazing panels of any size for various (architectural, automotive, aeronautical, railway) uses. In particular, the device and the method may advantageously be applied to the strip of flat glass on float line. They may also be applied to flat glazing panels intended for architectural applications or to special glazing panels intended for electronic applications (plasma or LCD displays, etc.) and to any other transparent substrate.

The present invention will now be described with the aid of purely illustrative examples that do not in any way limit the scope of the invention and on the basis of the appended illustrations in which:

FIG. 1 shows a schematic sectional view of an analysis device according to the invention for a measurement in transmission;

FIG. 2 illustrates an example of a reference pattern according to the invention; and FIG. 3 illustrates a reconstructed image of the substrate making a defect appear in its center.

FIGS. 1 and 2 have not been drawn to scale in order to make it easier to examine them.

The illumination system 4 may be a back-lighting system when the support panel 11 is translucent, such as a white plastic sheet. Preferably, the illumination system 4 then consists of numerous light-emitting diodes that are positioned to the rear of the translucent support panel.

As a variant, when the support panel 11 is opaque, the illumination system 4 is formed from a light source placed to the front of the reference pattern, for example a spot oriented so as to illuminate the front face of the panel supporting the reference pattern.

The camera 3 is a linear camera: it generates an image frame which, by digital processing, is stacked with the preceding frames to form an overall two-dimensional image of the moving substrate. Since the reference pattern is small compared with the substrate as will be seen, the substrate 2 or the reference pattern is able to be displaced in translation one relative to the other so as to ensure the requisite number of image acquisitions over the entire substrate. The frequency with which the camera is triggered for each image acquisition is slaved to the speed of displacement.

The camera is positioned at a suitable distance d so as to display the entire extent or a fraction of the substrate, which is transverse to the direction of displacement of the substrate or the reference pattern. Thus, if the displacement is in a horizontal plane, the camera is placed vertically.

The camera 3 could make an angle to the vertical adapted to the conditions of implantation on the industrial line.

The reference pattern 10, as illustrated in FIG. 2, is formed on a support 11 of oblong shape. It is unidirectional and consists of a pattern 10a.

The reference pattern according to the invention has a small extent that is small compared with the substrate to be measured. For example, for measuring a continuous substrate 0.80 m in width, the reference pattern extends over 5 cm by 1.0 m.

The pattern 10a of the reference pattern lies along the shorter extent of the support, being periodic transverse to the short extent, i.e. periodic along the long extent of the support.

The pattern 10a is composed of an alternating succession of light and dark sharply contrasting lines.

The processing/computation means 5 are connected to the camera so as to carry out the mathematical processing and analyses that follow the successive image acquisitions.

FIG. 3 illustrates an image recorded by the camera, the image of the reference pattern being distorted by the presence of defects in one direction. The implementation of the device consists in:
  using the camera, taking a linear image in transmission of the illuminated reference pattern, the substrate or the reference pattern moving, one relative to the other, along a single running direction parallel to the direction of the defects and to the lines of the reference pattern;
  (1) acquiring the row of pixels of the linear image taken along the long extent of the reference pattern, without moving the camera relative to the reference pattern;
  (2) applying digital processing to the acquired row of pixels in order to calculate a representative quantity, for each pixel, of the effect of the substrate on the light transmitted by the substrate, for example the optical power of each pixel;
  (3) displaying an image of the row of pixels in which the color of each pixel is representative of the optical power of the pixel;
  repeating the acquisition/processing/display cycle (1) (2) (3) several times in a periodic manner and stacking the images of the rows of pixels so as to reconstruct the image of a part of the substrate by simulating a continuous running effect that will correspond to the display in real-time of a 2D map of the defects; and
  analyzing the reconstructed image by digital processing so as to deduce therefrom the position of the defects and to quantify their gravity.

Acquisition of a series of n rows of pixels as the substrate runs past the reference pattern makes it possible to reconstruct, by simple stacking of rows, a single image in two dimensions. The Applicant has demonstrated that this type of reference pattern is particularly advantageous because of its limited size and its performance in detecting defects on a continuous ribbon obtained with the device.

It is possible to calculate, for each acquired line, the intensity of the optical defects. With this method, it is unnecessary to know the state of the preceding line, nor that of the next line.

However, to analyze the gravity of a defect it is necessary to see all of it and therefore to use an image consisting of many lines (a defect may last several minutes or even several hours). Each line is therefore "converted" into optical power and the 2D map of this optical power undergoes image processing in order to analyze the gravity of the defects. To summarize, the line undergoes signal processing, and the map undergoes image processing, this being particularly advantageous. The simplest image processing is a simple thresholding operation.

A reference pattern is a spatially periodic signal. The mathematical analysis consists in characterizing in a known manner this signal by its local phase modulo $2\pi$, at a pixel of the camera, and a two-dimensional map of the phases (corresponding to all the pixels) of the two-dimensional image seen in transmission, called a phase map, is thus defined.

This extraction of the phase map modulo $2\pi$ can be obtained using the following well known Fourier transform analysis technique.

This method is widely described in the literature. It can thus be divided into:
  acquisition of a linear image of the reference pattern distorted by the specimen;
  calculation of the Fourier transform of the pixel row (one-dimensional transform);
  automatic search for the characteristic peak of the fundamental frequency $f_0$ of the reference pattern;
  band-pass filtering using a Gaussian band-pass filter, or other such filter, of this fundamental frequency $f_0$. The effect of this filtering is to remove the continuous background of the image of the reference pattern and the harmonics of the signal of the reference pattern;
  shifting of the $f_0$ filtered spectrum so as to bring the characteristic peak of the image reference pattern to the frequency $0$. This shift causes the grid lines of the reference pattern to disappear, leaving only the distortions of the reference pattern;
  calculation of the inverse Fourier transform of the image, pixel column by pixel column. The image obtained reveals only the distortions. This image is a complex image comprising a real part R and an imaginary part I;
  calculation of the local phase at a pixel, modulo $2\pi$, of the image. This phase is obtained by calculating, pixel by pixel, the value of arctan (I/R).

Once the step of calculating the phase modulo $2\pi$ of the image has been carried out for each pixel, the map of the phase derivatives, also called a gradient map, is easily deduced therefrom. This calculation of the phase gradient of the image is obtained by simple difference of the phase pixel to pixel, the $2\pi$ phase jumps being easily eliminated. This calculation may be carried out after the acquisition of each of the lines or else on a group of lines.

After the phase map of the complete reconstructed image has been deduced from the series of linear images captured by the camera, it is then possible to link the derivative of the phase at each point of the image to the optical power Pi of the defects of the glazing panel causing these local phase variations using an optical calculation model that enables the optical power Pi to be calculated from the derivative of this phase. By determining the optical power and comparing it with a threshold value, it is possible to quantify the defect.

As a variant, the phase derivative will rather be able to be compared with a local calibration width that will provide a distortion width which is also representative of the magnitude of the defect.

By quantifying the defect, it is thus possible to establish the optical quality of a substrate directly on the production line.

Consequently, the method according to the invention for analyzing the substrate consists:

in capturing, using a linear camera, a series of linear images in transmission of a narrow single-pattern reference pattern on said substrate without the need, as in the prior art, for studied coupling of the reference pattern relative to the camera or for use of a projector and a large screen;

in extracting the local phases by digital processing, in calculating the derivative of these phases and in deducing, by mathematical calculation, the profile in intensity of the defects (preferably using an optical power calculation and its comparison with a threshold value);

in vertically stacking these profiles on a screen so as to reconstruct, row by row, an image of the map of the defects of the substrate; and in analysing this map so as automatically to detect therein the presence of defects beyond tolerated limits using conventional image processing techniques, such as the detection of edges or dynamic thresholding.

Finally, the proposed measurement device permits inspection over the entire length of the substrates present on an industrial line, without sampling the substrate, without either stopping or slowing down the substrate, without modifying its position on the conveying system and without using a system for projecting successive reference patterns without any optical or mechanical control constraints. The device uses a small area compared with the dimensions of the reference pattern, which are much smaller than the existing ones; typically, the support panel for the reference pattern of the invention is 1 meter in length by 5 cm in width.

The invention claimed is:

1. A device for analyzing a transparent surface of a substrate, comprising:
   a reference pattern formed on a support facing a surface of the substrate to be measured;
   a camera for capturing at least one image of the reference pattern distorted by the measured substrate;
   a reference pattern illumination system; and
   image processing/digital analysis means connected to the camera;
   wherein the support has an oblong shape of short and long extents, the reference pattern being unidirectional and including a pattern that lies along the short extent of the support, the pattern being periodic transverse to the short extent, and
   wherein the camera is linear and positioned to obtain a linear image in transmission of the reference pattern through the substrate along the long extent of the support.

2. The device as claimed in claim 1, in which the ratio of the long extent of the support to the small extent of the support is equal to or greater than 10, or is equal to or greater than 20.

3. The device as claimed in claim 1, in which the pattern comprises at least one line which has, along the short extent of the support, a width of between 0.1 mm and 5 cm, or between 1 mm and 2 mm.

4. The device as claimed in claim 1, in which the pattern includes an alternating succession of light and dark lines.

5. The device as claimed in claim 1, in which the support for the reference pattern includes a panel backlit by the illumination system.

6. The device as claimed in claim 5, in which the support is, on its face turned towards the panel to be measured, translucent and diffusing, or is a white plastic sheet.

7. The device as claimed in claim 1, in which the substrate is placed between the reference pattern and the camera for a measurement in transmission.

8. The device as claimed in claim 1, in which the support for the reference pattern is mounted to move relative to the substrate perpendicular to a plane in which the substrate runs.

9. The device as claimed in claim 8, further comprising a mechanical raising/lowering system for moving the support for the reference pattern further away from or closer to the substrate, while still maintaining sufficient sharpness of the image of the reference pattern captured by the camera.

10. The device as claimed in claim 1, further comprising a non-transitory memory in which computer executable instructions are recorded for:
    using the linear camera, taking a linear image in transmission of the illuminated reference pattern, the substrate or the reference pattern moving, one relative to the other, along a single running direction parallel to a direction of defects and to lines of the reference pattern;
    acquiring a row of pixels of the linear image taken along the long extent of the reference pattern, without moving the camera relative to the reference pattern;
    applying digital processing to the acquired row of pixels to calculate a representative quantity, for each pixel, of effect of the substrate on the light transmitted by the substrate, or optical power of each pixel;
    storing in memory values of the quantity for each pixel of the row, and displaying an image of the row of pixels in which a color of each pixel is representative of the quantity;
    repeating the acquisition/processing/display cycle plural times in a periodic manner and stacking images of the rows of pixels to reconstruct an image of a part of the substrate; and
    analyzing the reconstructed image by digital processing to deduce therefrom a position of the defects and to quantify their gravity.

11. Device according to claim 10, wherein the row acquisition period is longer than an acquisition time for each row, or is 0.1 seconds or longer.

12. A method of analyzing a transparent or specular surface of a substrate using a device comprising a reference pattern formed on a support of oblong shape of short and long extents, a linear camera for taking at least one image of the reference pattern distorted by the measured substrate, a reference pattern illumination system and image processing/digital analysis means connected to the camera, the method comprising:
    using the linear camera, taking a linear image in transmission of the illuminated reference pattern, the substrate or the reference pattern moving, one relative to the other, along a single running direction parallel to a direction of defects and to lines of the reference pattern;
    acquiring a row of pixels of the linear image taken along the long extent of the reference pattern, without moving the camera relative to the reference pattern;
    applying digital processing to the acquired row of pixels to calculate a representative quantity, for each pixel, of effect of the substrate on the light transmitted by the substrate, or optical power of each pixel;

storing in memory values of the quantity for each pixel of the row, and displaying an image of the row of pixels in which a color of each pixel is representative of the quantity;

repeating the acquisition/processing/display cycle plural times in a periodic manner and stacking images of the rows of pixels to reconstruct an image of a part of the substrate; and analyzing the reconstructed image by digital processing to deduce therefrom a position of the defects and to quantify their gravity.

13. The method as claimed in claim 12, in which each line is displayed after each applying digital processing so that the reconstructed image of a part of the substrate simulates a continuous running effect that will correspond to a display in real-time of a 2D map of the defects.

14. The method as claimed in claim 12, in which the substrate is a continuous glass ribbon.

* * * * *